US009759700B2

(12) United States Patent
Sjong et al.

(10) Patent No.: US 9,759,700 B2
(45) Date of Patent: Sep. 12, 2017

(54) GAS DETECTION DEVICE WITH GRAPHENE MEMBRANE

(71) Applicant: Empire Technology Development LLC, Wilmington, DE (US)

(72) Inventors: Angele Sjong, Louisville, CO (US); Kraig Anderson, Burlingame, CA (US); Gary L. Duerksen, Ward, CO (US); Seth Adrian Miller, Englewood, CO (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 277 days.

(21) Appl. No.: 14/005,232

(22) PCT Filed: Nov. 30, 2012

(86) PCT No.: PCT/US2012/067490
§ 371 (c)(1),
(2) Date: Sep. 13, 2013

(87) PCT Pub. No.: WO2014/084864
PCT Pub. Date: Jun. 5, 2014

(65) Prior Publication Data
US 2014/0154811 A1    Jun. 5, 2014

(51) Int. Cl.
*G01N 33/00* (2006.01)
*G01N 27/40* (2006.01)

(52) U.S. Cl.
CPC ......... *G01N 33/0016* (2013.01); *G01N 27/40* (2013.01); *Y10T 29/53* (2015.01);
(Continued)

(58) Field of Classification Search
CPC ............... G01N 33/0016; G01N 27/40; Y10T 436/207497; Y10T 436/153333;
(Continued)

(56) References Cited

U.S. PATENT DOCUMENTS

| 2011/0062422 A1 | 3/2011 | Ryu et al. |
| 2011/0200787 A1 | 8/2011 | Regan et al. |

(Continued)

FOREIGN PATENT DOCUMENTS

| WO | 2011119961 A2 | 9/2011 |
| WO | 2012121717 A1 | 9/2012 |

OTHER PUBLICATIONS

International Search Report and Written Opinion for PCT/US12/67490, Filed Nov. 30, 2012, mailed Feb. 19, 2013.
(Continued)

*Primary Examiner* — Rebecca M Fritchman
(74) *Attorney, Agent, or Firm* — Turk IP Law, LLC

(57) ABSTRACT

Technologies are generally described for gas filtration and detection devices. Example devices may include a graphene membrane and a sensing device. The graphene membrane may be perforated with a plurality of discrete pores having a size-selective to enable one or more molecules to pass through the pores. A sensing device may be attached to a supporting permeable substrate and coupled with the graphene membrane. A fluid mixture including two or more molecules may be exposed to the graphene membrane. Molecules having a smaller diameter than the discrete pores may be directed through the graphene pores, and may be detected by the sensing device. Molecules having a larger size than the discrete pores may be prevented from crossing the graphene membrane. The sensing device may be configured to identify a presence of a selected molecule within the mixture without interference from contaminating factors.

14 Claims, 8 Drawing Sheets

(52) U.S. Cl.
CPC .... *Y10T 436/153333* (2015.01); *Y10T 436/17* (2015.01); *Y10T 436/177692* (2015.01); *Y10T 436/182* (2015.01); *Y10T 436/186* (2015.01); *Y10T 436/204998* (2015.01); *Y10T 436/207497* (2015.01); *Y10T 436/21* (2015.01); *Y10T 436/22* (2015.01)

(58) Field of Classification Search
CPC ... Y10T 436/22; Y10T 436/17; Y10T 436/21; Y10T 29/53; Y10T 436/177692
USPC ......... 436/72, 101, 106, 116, 120, 122, 133, 436/136, 139, 144, 182; 204/415; 205/779.5, 780.5, 783, 786.5, 787, 793; 422/83; 73/24.01, 23.2
See application file for complete search history.

(56) References Cited

U.S. PATENT DOCUMENTS

| | | | |
|---|---|---|---|
| 2011/0201201 A1 | 8/2011 | Arnold et al. | |
| 2011/0261605 A1 | 10/2011 | Kioussis et al. | |
| 2012/0070612 A1 | 3/2012 | Lee et al. | |
| 2012/0183738 A1* | 7/2012 | Zettl | B81C 99/008 428/166 |
| 2012/0234679 A1 | 9/2012 | Garaj et al. | |
| 2012/0255899 A1* | 10/2012 | Choi | B01D 53/228 210/489 |
| 2012/0288433 A1 | 11/2012 | Sutter et al. | |
| 2012/0308846 A1 | 12/2012 | Lee et al. | |
| 2013/0192460 A1 | 8/2013 | Miller et al. | |
| 2014/0053651 A1* | 2/2014 | Besling | G01L 9/0042 73/702 |

OTHER PUBLICATIONS

Hubert, et al. "Hydrogen sensors—A Review"; Sensors and Actuators B 157 (2011) 329-352: available Apr. 29, 2011(Apr. 29, 2011), pp. 329, 330, 332, 334-336.

Wongwiriyapan, et al. "Hydrogen sensing properties of protective-layer coated single-walled carbon nanotubes with palladium nanoparticle decoration." College of Nanotechnology, King Mongkut's Institute of Technology Ladkrabang, Bankkok, Thailand; Nanotechnology, Feb. 4, 2011.

Boon-Brett, et. al., "Identifying performance gaps in hydrogen safety sensor technology for automotive and stationary applications", INt. J. Hydrogen Energy, vol. 35, 373-384; Jan. 2010.

Xu, et al., "Self-assembled monolayer-enhanced hydrogen sensing with ultrathin palladium films", Appl. Phys. Lett. 86, 203104; May 11, 2005.

Joshi, "Pd Nanoparticles and thin films for room temperature hydrogen sensor", Nanoscale Res Lett,4:1191-1196; published Jul. 1, 2009.

Wu, et. al., "Wafer-scale synthesis of graphene by CVD and its application in hydrogen sensing", Sensors and Actuators B 150 296-300; Jul. 16, 2010.

Du, et al., "Separation of hydrogen and nitrogen gases with porous graphene membrane", J. Phys. Chem. C.115, 23261-23266., Oct. 27, 2011.

Jiang, et. al., "Porous graphene as the ultimate membrane for gas separation", Nano Letters vol. 9, Issue 12, 4019-4024, Dec. 9, 2009.

Kumar, et. al., "Fast response and recovery of hydrogen sensing in Pd-Pt nanoparticle-graphene composite layers", Nanotechnology 22 275719; Published May 26, 2011.

"Zirconium-Aluminum", Getter Technologies Inernational, Ltd. www.getters.com/Zirconium-Aluminum.html; retrieved Sep. 9, 2013.

* cited by examiner

COMPUTER PROGRAM PRODUCT 800

SIGNAL BEARING MEDIUM 802

804 AT LEAST ONE OF

ONE OR MORE INSTRUCTIONS FOR PROVIDING A FLUID MIXTURE TO A GRAPHENE MEMBRANE INCLUDING DISCRETE PORES PROVIDING SIZE-SELECTIVE ACCESS OF GAS MOLECULES;

ONE OR MORE INSTRUCTIONS FOR CONTACTING THE FLUID MIXTURE TO THE GRAPHENE MEMBRANE;

ONE OR MORE INSTRUCTIONS FOR SELECTIVELY PERMEATING A MOLECULE THROUGH THE GRAPHENE MEMBRANE;

ONE OR MORE INSTRUCTIONS FOR PROVIDING A SENSING DEVICE CONFIGURED TO DETECT THE MOLECULE; AND

ONE OR MORE INSTRUCTIONS FOR DETECTING A PRESENCE OF MOLECULE AT THE SENSING DEVICE.

| COMPUTER-READABLE MEDIUM 806 | RECORDABLE MEDIUM 808 | COMMUNICATIONS MEDIUM 810 |

FIG. 8

GAS DETECTION DEVICE WITH GRAPHENE MEMBRANE

CROSS-REFERENCE TO RELATED APPLICATION

This Application is the U.S. National Stage filing under 35 U.S.C §371 of International Application No. PCT/US12/67490 filed on Nov. 30, 2012.

BACKGROUND

Unless otherwise indicated herein, the materials described in this section are not prior art to the claims in this application and are not admitted to be prior art by inclusion in this section.

The emergence of a proliferous use of hydrogen in a variety of industries motivates sensing devices that can reliably detect the presence of hydrogen, an explosive gas. Some factors that may be considered when choosing sensing devices may include power consumption, lifetime, and sensitivity to selected molecules. Sensing devices can be developed to be highly sensitive to hydrogen; however, the sensitivity of the sensing devices may be diminished due to factors such as temperature, humidity, and interference by the presence of contaminating molecules.

SUMMARY

The following summary is illustrative only and is not intended to be in any way limiting. In addition to the illustrative aspects, embodiments, and features described above, further aspects, embodiments, and features will become apparent by reference to the drawings and the following detailed description.

The present disclosure generally describes compositions, methods, apparatus, systems, devices, and/or computer program products related to manufacturing or using perforated graphene, for example, as part of membrane which may be used for selective gas detection employing a graphene membrane.

According to some examples embodiments, the present disclosure describes a gas detection device. The gas detection device may include a substrate, a sensing device coupled to the substrate, the sensing device configured to detect a presence of one or more gases, and a graphene membrane coupled to the sensing device, the graphene membrane including a plurality of discrete pores having a size-selective to pass of the one or more gases across the graphene membrane such that the sensing device may be operable to detect the presence of the one or more gases.

According to other example embodiments, the present disclosure also describes various methods of detecting a gas molecule in a fluid mixture including one or more gases. An example method may include exposing the fluid mixture, which includes at least a first gas molecule and a second gas molecule to a graphene membrane such that the fluid mixture may be brought in contact with the graphene membrane, where the graphene membrane includes a plurality of discrete pores having a size-selective for the passage of the first gas molecule but not the second gas molecule, selectively permeating the first gas molecule through the discrete pores of the graphene membrane, detecting the first gas molecule with a sensing device, and/or identifying the presence of the first gas molecule with sensing device.

According to further example embodiments, the present disclosure also includes various methods of forming a gas detection device. An example method may include providing a substrate to provide support a sensing device and a graphene membrane, coupling the sensing device with the substrate, where the sensing device may be operable to detect a presence of one or more gases included in a fluid mixture, and/or coupling the graphene membrane with the sensing device, where the graphene membrane includes a plurality of discrete pores having a size-selective for the passage of the one or more gases across the graphene membrane for detection by the sensing device.

According to yet other example embodiments, the present disclosure also describes a system for manufacturing a gas detection device. The system may include a controller configured by instructions stored thereon to facilitate manufacturing of the gas detection device employing a graphene source, a substrate source, and a sensing device applicator. The controller may be operable to configure the graphene source to provide a graphene membrane, where the graphene membrane includes a plurality of discrete pores having a size-selective for the passage of one or more gases included in a fluid mixture across the graphene membrane, configure the substrate source to provide a substrate to support the graphene membrane, and configure the sensing device applicator to contact a sensing device with the substrate, where the sensing device is configured to detect a presence of the one or more gases contained in the fluid mixture that cross the graphene membrane.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 8 illustrates a block diagram of an example computer program product that may be used to control the automated system of FIG. 5 or similar manufacturing equipment in making an example membrane, all arranged in accordance with at least some embodiments as described herein.

DETAILED DESCRIPTION

Figure 1:
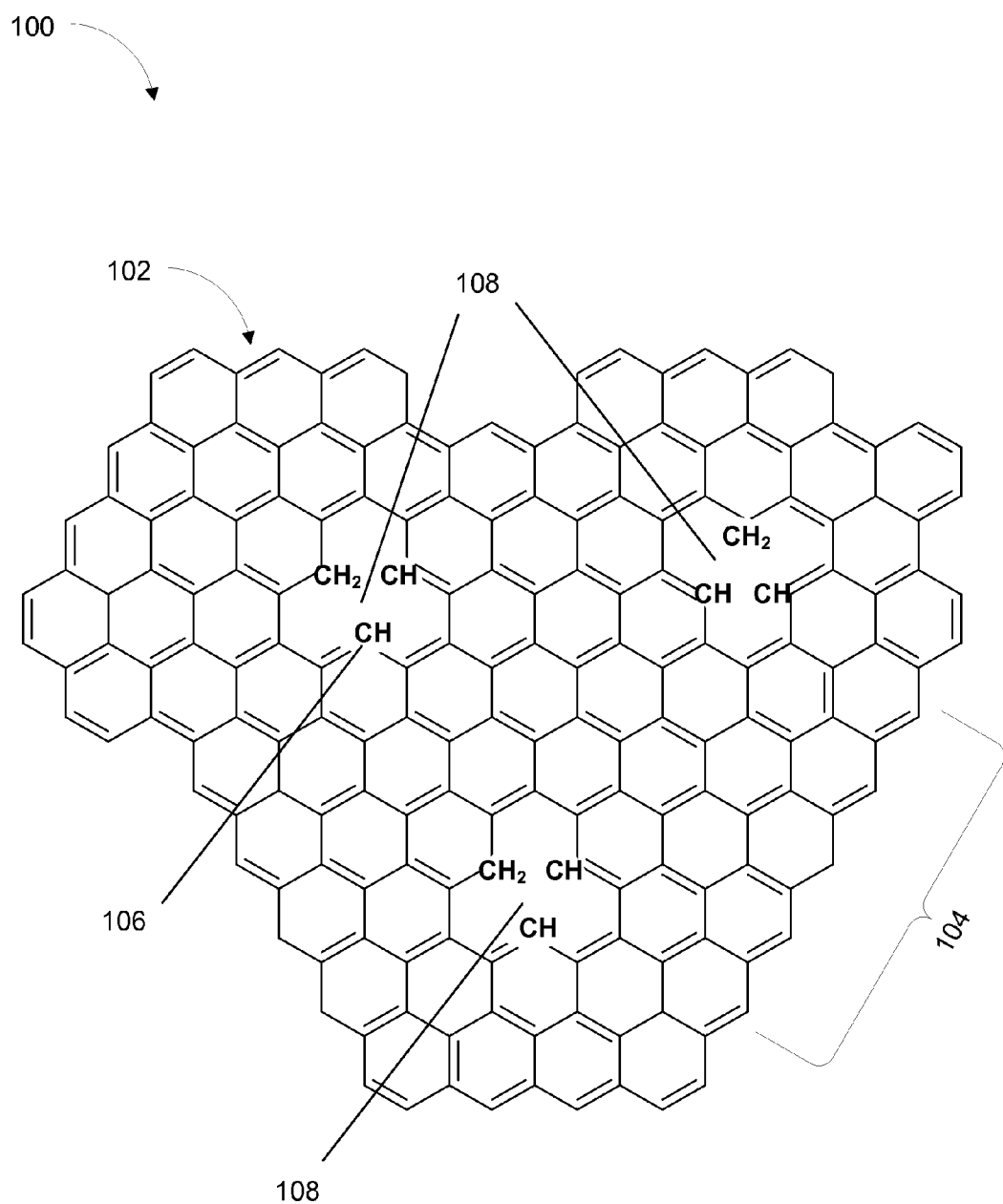
FIG. 1 is a conceptual drawing of an example perforated graphene monolayer.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to compositions, methods, apparatus, systems, devices, and/or computer program products related to manufacturing or using perforated graphene, for example, as part of membrane which may be used in gas separation.

Briefly stated, technologies are generally described for gas filtration and detection devices. Example devices may include a graphene membrane and a sensing device. The graphene membrane may be perforated with a plurality of discrete pores having a size-selective to enable one or more molecules to pass through the pores. A sensing device may be attached to a supporting permeable substrate and coupled with the graphene membrane. A fluid mixture including two or more molecules may be exposed to the graphene membrane. Molecules having a smaller diameter than the discrete pores may be directed through the graphene pores, and may be detected by the sensing device. Molecules having a larger size than the discrete pores may be prevented from crossing the graphene membrane. The sensing device may be configured to identify a presence of a selected molecule within the mixture without interference from contaminating factors.

The following definitions are intended to be general definitions for helping the reader understand the disclosure. Any meanings implied throughout the specification are not intended to be limiting, but are intended to be example non-literal definitions for describing some example embodiments.

As used herein, "graphene" may mean a planar allotrope of carbon characterized by a hexagonal lattice of carbon atoms that may be connected by aromatic carbon-carbon bonds. As used herein, a graphene "monolayer" may be a one-carbon atom thick layer of graphene. In some examples, the graphene monolayer may include some nonaromatic carbons, e.g., some carbons may be passivated with hydrogen and may be bonded to other carbons by nonaromatic single carbon-carbon bonds. As used herein, a "perforated graphene monolayer" may mean a graphene monolayer that may include a plurality of discrete pores through the graphene monolayer. The discrete pores may pass entirely through the graphene monolayer. The discrete pores may permit selective passage of atomic or molecular species from one side of the graphene monolayer to the other side of the graphene monolayer. As used herein, a "chemically perforated" pore in the graphene may be characteristic of preparation by selective removal of one or more carbon atoms from the graphene lattice, for example, atomic or molecular species may be reacted with the graphene in a process which results in selective removal of one or more carbon atoms from the graphene lattice.

As used herein, the "minimum steric separation" may mean the distance between the centers of adjacent discrete pores. For example, a minimum steric separation corresponding to at least one intervening carbon-carbon bond may be at least about 1 Angstrom. In some examples, a minimum steric separation corresponding to at least one intervening six-membered graphene ring may be at least about 2.4 Angstroms. In various examples, a minimum steric separation may range from between about 1 Angstrom to about 100 Angstroms, for example, at least about 1, 2, 3, 4, 5, 6, 7, 8, 9, 10, 12.5, 15, 20, 25, 35, or 50 Angstroms.

As used herein, "discrete" pores in a graphene monolayer may be distinct from each other by at least one intervening carbon-carbon bond, or in some examples, at least one intervening six-membered graphene ring. For example, two discrete pores may be separated from each other by at least one intervening six-membered graphene ring or at least one intervening carbon-carbon bond.

As used herein, a "carbon vacancy defect" may be a pore in a graphene monolayer which may be defined by the absence of one or more carbon atoms compared to a graphene monolayer without a carbon vacancy defect. As used herein, the "number" of carbon vacancy defects in reference to "substantially the same number of one or more carbon vacancy defects" may mean about one or more carbon defects, or in some examples about two or more carbon defects. In various examples, the number of carbon vacancy defects may be between about one and about ten defects, for example, about: one, two, three, four, five, six, seven, eight, nine, or ten defects.

As used herein, a "substantially uniform pore size" may mean that the discrete pores may be characterized by substantially the same number of one or more carbon vacancy defects per discrete pore. In various examples, discrete pores of substantially uniform pore size may have their carbon vacancy defects arranged in substantially the same relative lattice positions within each discrete pore. For example, a plurality of substantially uniform pores that include six carbon vacancy defects each may correspond to removal of a six membered ring of carbon atoms in the hexagonal graphene lattice. In another example, a plurality of substantially uniform pores that include six carbon vacancy defects each may correspond to removal of a six membered staggered linear chain of carbon atoms in the hexagonal graphene lattice.

As used herein, "substantially uniform pore sizes throughout" may mean that at least about 80% of the discrete pores in a perforated graphene monolayer may have a substantially uniform pore size. In various examples, the percentage of discrete pores in a perforated graphene monolayer that may have a substantially uniform pore size may be: about 85%, about 90%, about 95%, about 96%, about 97%, about 98%, about 99%, about 99.5%, or about 99.9%. In some examples, all of the discrete pores in a perforated graphene monolayer may have a substantially uniform pore size.

As used herein, "substantially the same number of one or more carbon vacancy defects" in relation to the plurality of discrete pores may mean that such discrete pores differ from each other by at most about three carbon vacancy defects. For example, a plurality of pores having substantially the same number of one or more carbon vacancy defects may range between one and three carbon vacancy defects per pore. In various examples, discrete pores may vary in number of carbon vacancy defects by about three, about two, or about one. In some examples, each of the plurality of discrete pores has the same number of carbon vacancy defects.

As used herein, "separation efficiency" may mean a ratio of perforated graphene membrane permeability rates between specific pairs of atomic or molecular species. For example, the perforated graphene monolayer as described below in conjunction with FIG. 1 and FIG. 2 may be characterized by a hydrogen/methane separation efficiency, which may be a ratio of permeation rates of molecular hydrogen ($H_2$) compared to methane ($CH_4$). In some examples, the hydrogen/methane separation efficiency may be at least about 200:1; or in various examples, between about 200:1 and about $10^{23}$:1, for example, at least about: $10^3$:1; $10^4$:1; $10^5$:1; $10^6$:1; $10^9$:1; $10^{12}$:1; $10^{15}$:1; $10^{18}$:1; or $10^{21}$:1. Some example separation efficiency theoretical calculations for a one-atom thick graphene membrane characterized by pores 2.5 Angstroms in diameter provide that the ratio of a calculated hydrogen permeability rate divided by a calculated methane permeability rate is $10^{23}$:1. In comparison, currently known "solution diffusion" polymer membranes have a hydrogen to methane separation efficiency of about 150:1.

As used herein, a "permeable substrate" may be any material that may be employed to provide support to a perforated graphene monolayer. As used herein, a "permeable substrate" may also be permeable to at least one atomic or molecular species that traverses discrete pores in the perforated graphene monolayer. Suitable substrates may include "solution-diffusion" solid membranes that permit atomic or molecular species to diffuse through the solid material of the permeable substrate. Suitable permeable substrates may also be configured as porous membranes or filters having pores, voids, channels, or the like, through which atomic or molecular species may travel. Suitable materials for the substrate may include, for example, one or more of $SiO_2$, SiC, Si, polyethylene, polypropylene, polyester, polyurethane, polystyrene, polyolefin, polysulfone and/or polyethersulfone. In various examples, suitable materials for the permeable substrate may be characterized by a minimum molecular weight cutoff from: about 1,000 Daltons to about 1,000,000 Daltons; about 5,000 Daltons to about 1,000,000 Daltons; about 25,000 Daltons to about 500,000 Daltons; about 50,000 Daltons to about 250,000 Daltons; or about 100,000 Daltons. In some examples, a suitable permeable substrate may include a polyether sulfone membrane characterized by a maximum molecular weight cutoff of about 100,000 Daltons.

As used herein, a "fluid mixture" may be any fluid phase, e.g., gas phase, liquid phase, or supercritical phase, which may include at least a first molecular species and a second molecular species. In various examples, the fluid mixture may include: a mixture of gases; a mixture of a vapor in a gas; a mixture of liquids; a solution of a gas dissolved in a liquid; a solution of a solid dissolved in a liquid; a solution of a gas, liquid or solid in a supercritical fluid; or the like. In some examples, the fluid mixture may be in contact with other phases of the two or more different molecules. For example, a fluid mixture that includes fluid phase carbon dioxide as one of the molecules may be in contact with solid phase carbon dioxide.

FIG. 1 is a conceptual drawing of an example perforated graphene monolayer, arranged in accordance with at least some embodiments described herein. Diagram 100 generally illustrates the hexagonal lattice of carbon atoms 106 and aromatic bonds characteristic of graphene. The placement of the carbon-carbon double bonds in example graphene monolayers described herein, for example, in the graphene monolayer 102, is intended to be illustrative of graphene and is not intended to be limiting.

The graphene monolayer 102 may be chemically perforated with a plurality of discrete pores 108. The discrete pores 108 may be formed by the removal of at least one carbon atom from a plurality of locations in the graphene monolayer 102. The discrete pores 108 may have a substantially uniform pore size characterized by at least one carbon vacancy defect in the graphene monolayer 102. In various examples, each discrete pore 108 may include hydrogen-passivated carbon atoms 106. Diagram 100 also shows a minimum steric separation 104 between adjacent discrete pore 108 locations in example graphene monolayer 102.

Figure 2:
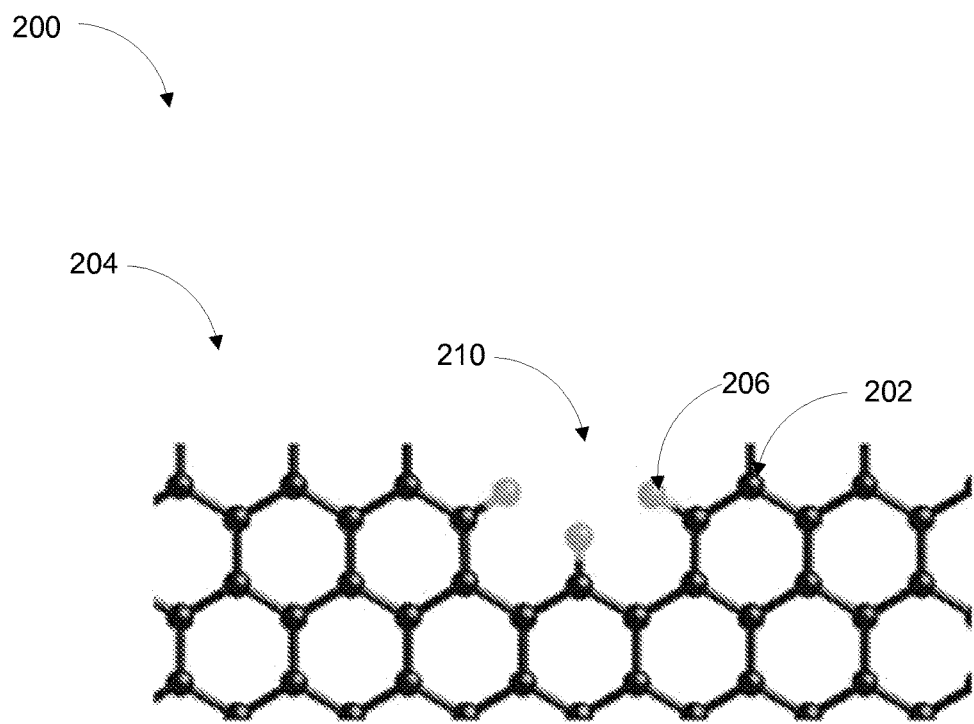
FIG. 2 illustrates an example graphene monolayer showing passivated pores of the graphene monolayer.

FIG. 2 illustrates an example graphene monolayer showing passivated pores of the graphene monolayer, arranged in accordance with at least some embodiments described herein. Diagram 200 illustrates a graphene monolayer 204 including a plurality of discrete pores 210. The discrete pores 210 may be formed by selective removal of one or more carbon atoms 202 from the hexagonal graphene lattice, causing a plurality of carbon vacancy defects, such that each discrete pore 210 in the graphene monolayer 204 may be characterized by the absence of at least one carbon atom 202. The carbon atoms 202 may be removed employing one or more of atomic oxygen etching, electron beam etching, or selective chemical etching techniques. Other techniques may include UV-induced oxidative etching, ion beam etching and/or lithographic masking coupled with oxygen plasma etching. In some examples, the remaining carbon atoms 202 at the pore may be passivated with hydrogen atoms 206 to provide structural stability.

The discrete pores 210 may extend through the graphene monolayer 204 such that the discrete pores 210 may permit selective passage of atomic or molecular species from one side of the graphene monolayer 204 to the other side of the graphene monolayer 204. Each of the discrete pores 210 may have a substantially uniform pore size and may be characterized by a range of between about one carbon vacancy defect and about ten carbon vacancy defects. The discrete pores 210 of the graphene membrane may be of a selected size to provide a separation efficiency between a first molecular species and a second molecular species by enabling the passage of at least the first molecular species and preventing passage of the second molecular species. For example, the discrete pores 210 may have a diameter in a range from about 2 to about 3 Angstroms such that the discrete pores 210 are selective for the passage of hydrogen.

Figure 3:
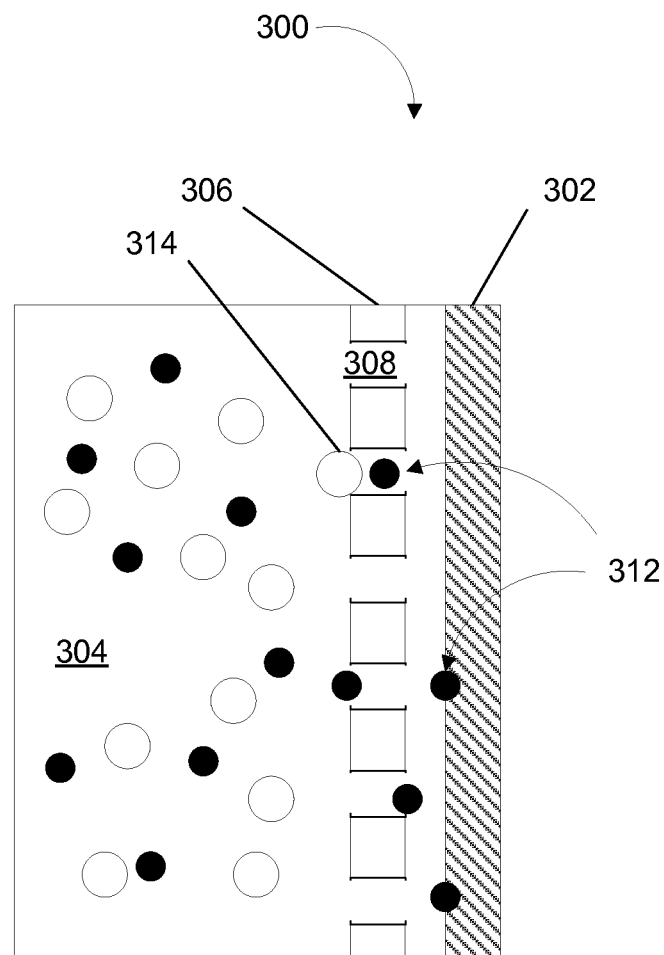
FIG. 3 is conceptual drawing of a side view of an example membrane illustrating a method of separating a gas mixture of two molecules.

FIG. 3 is a conceptual drawing of a side view of an example membrane illustrating a method of separating a gas mixture of two molecules, arranged in accordance with at least some embodiments described herein. Diagram 300 includes fluid mixture 304 that includes molecules 312, 314, graphene monolayer 306 that includes discrete pores 308, and substrate 302.

An example membrane may be a perforated graphene monolayer 306. A fluid mixture 304 may include two or more molecules 312, 314 which may be exposed to the graphene monolayer 306 to separate the fluid mixture 304. The example perforated graphene monolayer 306 may include discrete pores 308 configured to enable one or more of the molecules to pass through the discrete pores 308 to separate the molecules within the fluid mixture. The graphene monolayer 306 may be coupled with substrate 302 to support the graphene monolayer 306. The substrate 302 may be permeable or non-permeable. The graphene monolayer 306 may be coupled with the substrate 302 through an intermediate spacer, such as an insulating frame and/or electrode contacts.

In diagram 300, the graphene monolayer 306 may be exposed to the fluid mixture 304 including first molecule 312, symbolized by dark-filled circles, and second molecule 314, symbolized by white-filled circles. The first and second molecules may also include one or more differences in atomic or chemical character such as differences in elemental composition, isotopic composition, molecular structure, size, mass, hydrophobicity, polarity, polarizability, charge distribution, or the like. For example, the first molecule 312 may be smaller than the second molecule 314 as symbolized by the relative sizes of the filled circles in FIG. 3. In some examples, discrete pores such as 308 may be characterized by a diameter that may be selective for passage of the first molecule compared to the second molecule. The diameter of each pore may be selective for passage of first molecule 312 compared to second molecule 314 based on the one or more differences in atomic or chemical character, e.g., size. In some examples, the graphene monolayer 306 may be selective for the passage of hydrogen such that the graphene monolayer 306 may be characterized by a hydrogen/methane separation efficiency. The diameter may be about 2.5 Angstroms for enabling the passage of hydrogen through the discrete pores 308. In some examples, the diameter may be up to about 10 Angstroms for enabling separation of Hydrogen from other gases.

As demonstrated in diagram 300, the fluid mixture of molecules 312 and 314 may be contacted to the graphene monolayer 306, and the first molecule 312 may be directed through the discrete pores 308 to separate the first molecule 312 from the second molecule 314. The first molecule 312 may be directed through discrete pores 308 by imposing a gradient or differential across the graphene monolayer in a property that may cause the molecule to move through the discrete pores. The gradient or differential may include differences in one or more properties such as temperature, pressure, concentration, or electrochemical potential. For example, a temperature gradient may be established by heating or cooling molecules on one side of the membrane compared to the other side of the membrane. Similarly, a pressure gradient may be established by pressurizing or depressurizing one side of the membrane compared to the other side. A concentration gradient may be established, for example, by holding a mixture of gases to be separated on one side of the membrane, e.g., hydrogen and methane, and removing the desired molecule, e.g., hydrogen, from the other side of the membrane as it traverses the membrane. An electrochemical gradient may be established by using the membrane as a cell separator in an electrochemical cell, for example, separating the cathode and anode in water to hydrogen and oxygen electrolysis cell.

The first and second molecules may include compounds consisting of a single atom, for example, helium, neon, argon, krypton, xenon, and radon. The molecules may also include compounds of two or more atoms connected by one or more covalent bonds, ionic bonds, coordination bonds, or the like. For example, suitable molecules may include water, hydrogen, nitrogen, oxygen, carbon monoxide, carbon dioxide, sulfur dioxide, hydrogen sulfide, a nitrogen oxide, a C1-C4 alkane, a silane, or a haloacid.

In some examples, the second molecule may be a liquid, e.g., water or an organic solvent, and the first molecule may be a covalent or ionic molecular compound dissolved in the liquid. In some examples, one molecule may be a polar liquid such as water, and the other molecule may be a salt that includes a cation and an anion. Examples of cations for salts may include metal cations, e.g., alkali metal cations such as lithium, sodium, potassium, or the like; alkali earth metal cations such as calcium or magnesium, or the like; cations of transition metals such as copper, iron, nickel, zinc, manganese, or the like; cations of metals in other groups, such as cations of aluminum; and so on. Examples of anions for salts may include, but are not limited to, fluoride, chloride, bromide, iodide, chlorate, bromate, iodate, perchlorate, perbromate, periodate, hydroxide, carbonate, bicarbonate, sulfate, phosphate, and so on. In some examples, the fluid mixture may be a natural water source such as seawater or groundwater, where the perforated graphene membrane may be employed to separate water from natural solutes, such as sodium chloride, and/or unnatural solutes, such as molecules that are manmade pollutants.

Figure 4:
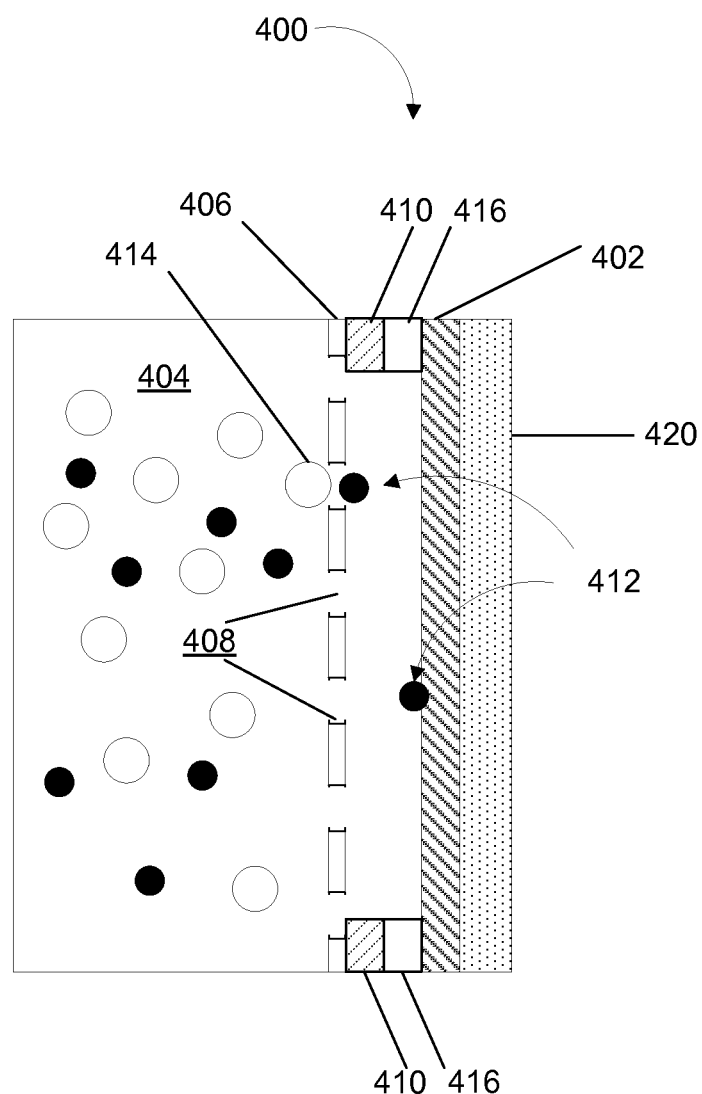
FIG. 4 is a conceptual drawing of a side view of an example membrane that includes an example perforated graphene monolayer in contact with a sensing device and a permeable substrate for detecting a gas molecule in a gas mixture.

FIG. 4 is a conceptual drawing of a side view of an example membrane that includes an example perforated graphene monolayer in contact with a sensing device and a permeable substrate configured to detect a gas molecule in a gas mixture, arranged in accordance with at least some embodiments described herein. Diagram 400 includes fluid mixture 404 that includes molecules 412, 414, graphene monolayer 406 that includes discrete pores 408, insulating frame 410, electrode contacts 416, sensing device 402, and substrate 420.

As illustrated in diagram 400, a membrane may be provided for separating a fluid mixture 404 including two or more molecules 412, 414. The membrane may be a graphene monolayer 406, which may be perforated with a plurality of discrete pores 408. The discrete pores 408 may permit one or more of the molecules to cross the graphene monolayer 406 through the discrete pores 408 to separate the molecules 412, 414 of the fluid mixture 404. A sensing device 402 may be provided to detect the presence of one or more molecules that cross the graphene monolayer 406. A permeable substrate 420 may be coupled to the sensing device 402 and the graphene monolayer 406 for support. The sensing device 402 may be coupled with the graphene monolayer 406 by insulating frame 410 and electrode contacts 416. The sensing device may be bonded to the substrate through non-covalent interactions, such as van der Waals forces, through adhesive interactions, such as via epoxy, pressure sensitive adhesive, or other bonding agents, and also employing mechanical fixation, for example by compressing the edges of the membrane to the substrate using a frame.

As illustrated in diagram 400, the sensing device 402 may be configured to detect a presence of one or more molecules that permeate the graphene monolayer 406. When the sensing device 402 is used to detect the presence of a selected molecule, the sensing device 402 may be subject to contamination from factors temperature, humidity, and contaminating molecules that reduce the sensitivity of the sensing device 402. The sensing device 402 may be coupled with the graphene monolayer 406 to protect the sensing device 402 from contamination due to various factors. The graphene monolayer 406 may protect the sensing device 402 from contamination by inhibiting the passage of molecules of a selected size across the graphene monolayer 406 such that certain molecules are prevented from contacting the sensing device 402. In order to inhibit larger contaminating molecules from contacting the sensing device 402, the graphene monolayer 406 may be perforated with a plurality of discrete pores 408 that may enable the passage of molecules of a selected size across the graphene monolayer 406 while inhibiting the passage of larger molecules. For example, the discrete pores may be of a size to provide size-selective access of a first molecule 412 having a diameter less than a diameter of the discrete pore 408, but not the second molecule 414 having a diameter greater than a diameter of the discrete pore 408.

In an example embodiment, the discrete pores 408 of the graphene monolayer 406 may have a size-selective to pass small molecules across the graphene monolayer, such that the sensing device may detect the presence of the small molecules as they cross the graphene monolayer 406 by passing through the discrete pores 408. For example, the discrete pores 408 may be of a selected size for enabling the passage of hydrogen such that the graphene monolayer 406 may be characterized by a selectivity for hydrogen. The graphene monolayer 406 may also be characterized by a selectivity for other small molecules including helium, neon, argon, xenon, krypton, radon, hydrogen, nitrogen, oxygen, carbon monoxide, carbon dioxide, sulfur dioxide, hydrogen sulfide, a nitrogen oxide, a C1-C4 alkane, a silane, or a haloacid.

In some examples, the sensing device 402 may be configured to detect the presence of hydrogen. Methane may be an example contaminating molecule in the detection of hydrogen by the sensing device 402. The graphene monolayer 406 may be characterized by a hydrogen/methane separation efficiency to enable the sensing device 402 to detect the presence of hydrogen without contamination due to the presence of methane. The discrete pores 408 may be of a selected size for enabling the passage of hydrogen across the graphene monolayer 406 while preventing the passage of methane. For example, the discrete pores 408 may have a diameter of about 2.5 Angstroms such that the discrete pores 408 are selective for the passage of hydrogen.

In some examples, the sensing device 402 may be selected from one or more of a metal-oxide sensor, a non-metal oxide sensor, a catalytic sensor, an optical sensor, or an electrochemical sensor configured to detect the presence of a selected molecule. The sensing device 402 may also be selected from one or more of, a resistance-based, thermally conductive, work function-based, mechanical, and/or acoustic sensor. In some examples, the sensing device 402 may be a rigid graphene sensor configured to detect the presence of hydrogen. Palladium nanoparticles may be deposited on the rigid graphene sensor to increase the sensitivity to identify the presence of hydrogen. The rigid graphene sensor may be coupled to the permeable substrate which may support the rigid graphene sensor. In other examples, the rigid sensor may be affixed within a depressed portion of the substrate. In an example embodiment, a portion of the surface of the substrate may be depressed such that a cavity is formed on the surface of the substrate. The sensor may be positioned within the cavity such that when the sensor is in position, the sensor may not extend beyond the surface of the substrate.

In an example scenario, the presence of a selected molecule in a fluid mixture may be detected as described hereafter. The fluid mixture 404 of molecules 412 and 414 may be exposed to the graphene monolayer 406. The first molecule 412 may be passed through the discrete pores 408 to separate the first molecule 412 from the second molecule 414, and to enable the sensing device to detect the presence of the first molecule 412 without contamination from the second molecule 414. The first molecule 412 may pass through the discrete pores 408 by an imposed gradient across the graphene monolayer 406. The gradient may include differences in one or more properties such as temperature, pressure, concentration, polarity, or electrochemical potential. As the first molecule 412 passes the graphene monolayer 406 through the discrete pores 408, the sensing device 402 may detect the first molecule 412 and identify the presence of the first molecule 412.

Figure 5:
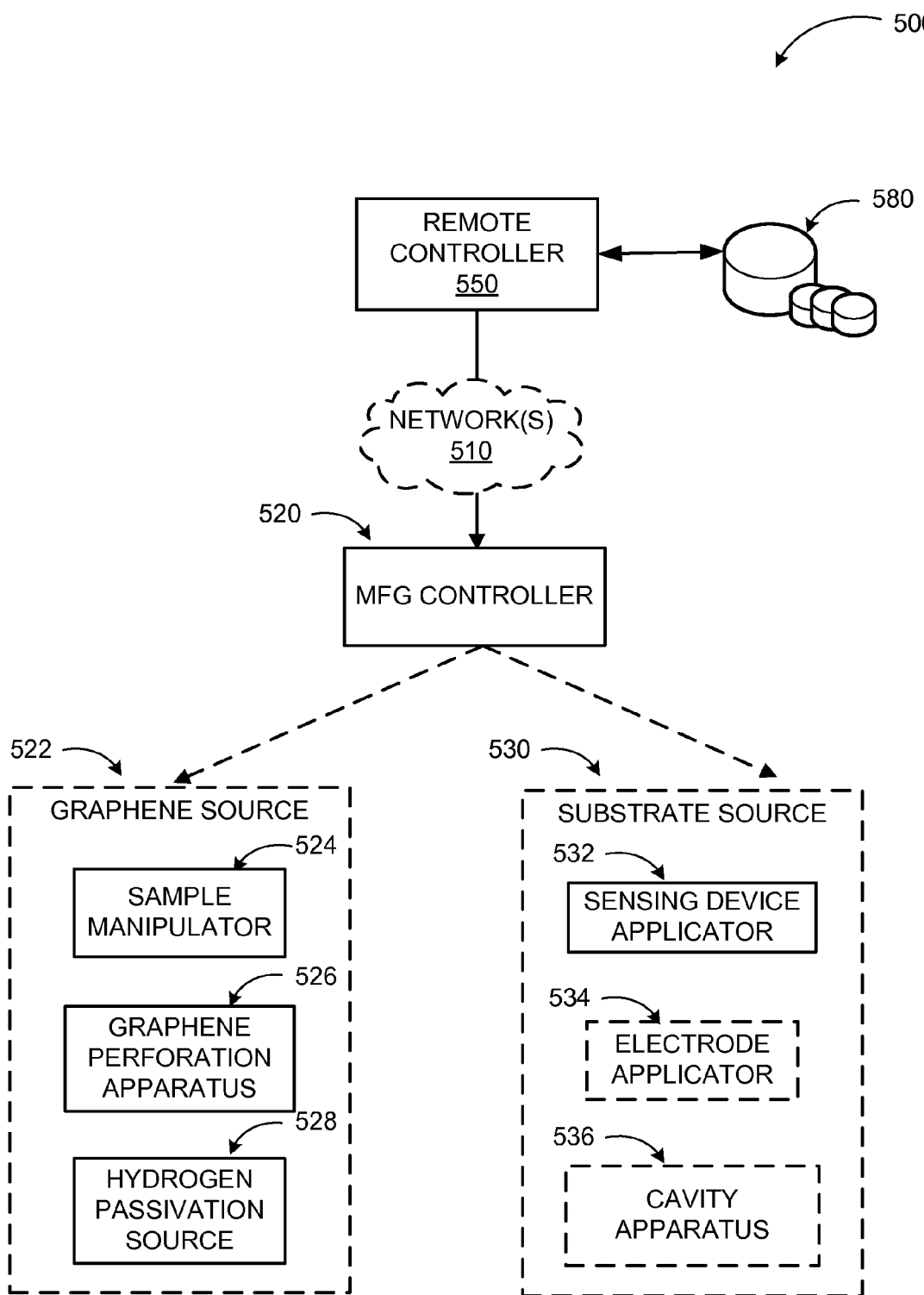
FIG. 5 is a block diagram of an automated system that may be used for making an example gas filtration and detection device.

FIG. 5 is a block diagram of an automated system that may be used for making an example gas filtration and detection device, arranged in accordance with at least some embodiments described herein.

System 500 may include a manufacturing controller 520, a graphene source 522, a sample manipulator 524, graphene perforation apparatus 526, a hydrogen passivation source, 528, a substrate source 530, a sensing device applicator 532, an electrode applicator 534, and a cavity apparatus 536.

As illustrated in system 500, a gas filtration and detection device may be manufactured to filter a fluid mixture and detect molecules that cross the graphene membrane. The manufacturing controller 520 may be coupled to machines that can be used to carry out steps for manufacturing the gas filtration and detection device including the graphene membrane and the sensing device, for example, the graphene source 522 to provide the graphene membrane and the substrate source 530 to provide a substrate and sensing device. The manufacturing controller 520 may be operable to configure the sample manipulator 524, graphene perforation apparatus 526, and hydrogen passivation source associated with the graphene source 522 to facilitate the formation of the graphene monolayer that includes a plurality of discrete pores. The manufacturing controller 520 may also be operable to configure a sensing device applicator 532, the electrode applicator 534, and the cavity apparatus 536 to facilitate contacting the graphene monolayer with a sensing device and a supporting substrate.

The manufacturing controller 520 may also configure the sample manipulator 524 to support the graphene monolayer during a process of forming the discrete pores in the graphene monolayer. The manufacturing controller 520 may also configure the graphene perforation apparatus 526 to facilitate formation of discrete pores in the graphene monolayer. The graphene perforation apparatus 526 may employ one or more of atomic oxygen etching, electron beam etching, or selective chemical etching for removing one or more carbon atoms from a plurality of locations within the carbon nanotubes causing a plurality of carbon vacancy defects in the carbon nanotubes. The manufacturing controller 520 may also configure the hydrogen passivation source 528 to facilitate passivating carbon atoms remaining at the one or more carbon vacancy defects in the graphene monolayer with hydrogen.

After forming the graphene monolayer with a plurality of discrete pores, the gas filtration and detection device, which includes the sensing device may be manufactured. The substrate source may provide a substrate on which a sensing device may be attached. The substrate may be permeable or non-permeable. The sensing device applicator 532 may provide the sensing device to couple the sensing device with the permeable substrate. In some examples, a cavity apparatus 536 may form a cavity in the permeable substrate by carving out a portion of the surface of the substrate such that the carved out portion is depressed and forms a cavity. The sensing device applicator 532 may affix the sensing device within the cavity formed in the permeable substrate. The substrate source 530 and the graphene source 522 may contact the graphene monolayer with the substrate and attached sensing device. The electrode applicator 534 may provide electrode contacts and an insulating frame for contacting the sensing device and substrate with the graphene monolayer.

Figure 6:
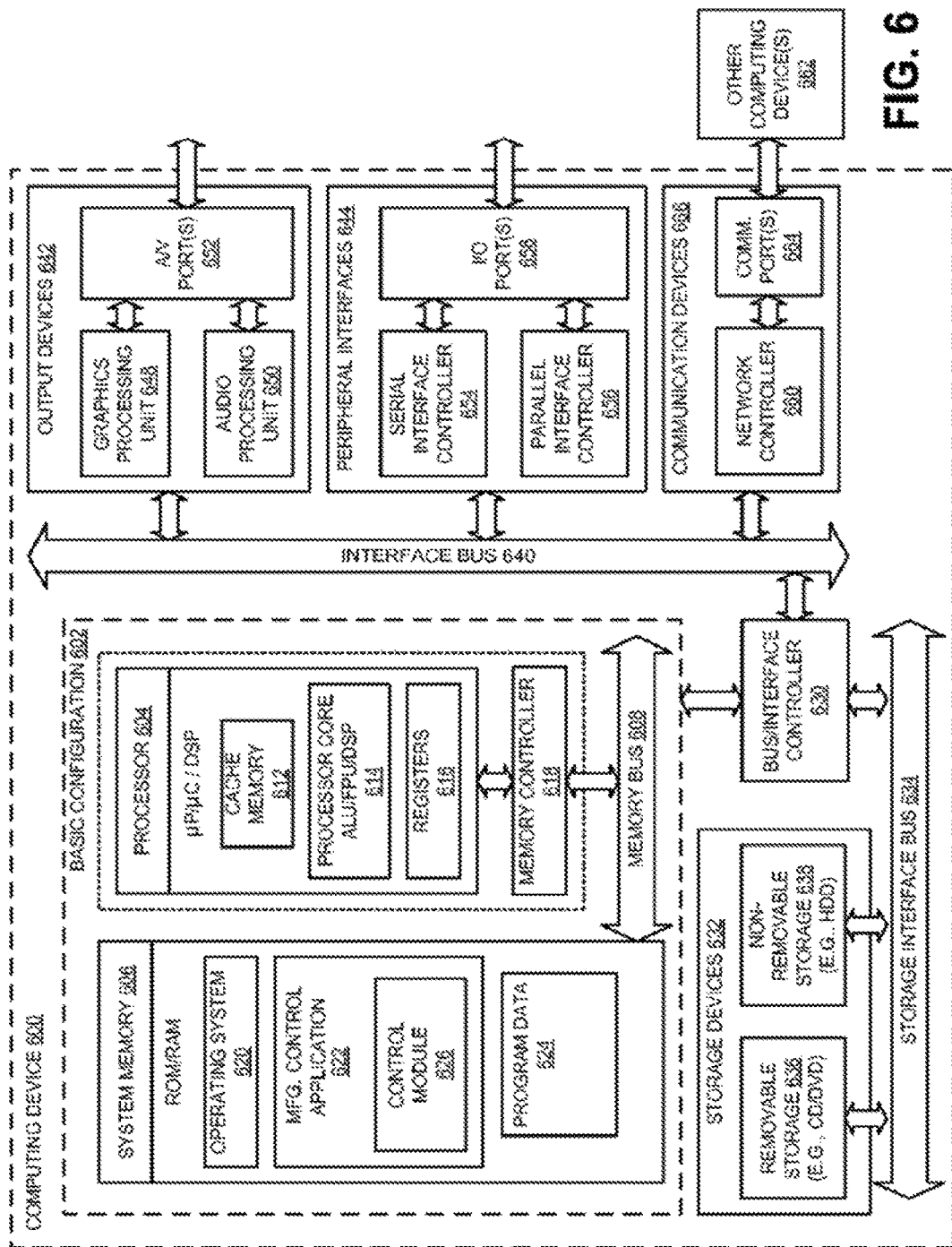
FIG. 6 illustrates a general purpose computing device that may be used to control the automated system of FIG. 5 or similar manufacturing equipment in making an example membrane.

FIG. 6 illustrates a general purpose computing device that may be used to control the automated system of FIG. 5 or similar manufacturing equipment in making an example membrane, arranged in accordance with at least some embodiments described herein. In a basic configuration 602, computing device 600 may include one or more processors 604 and a system memory 606. A memory bus 608 may be used for communicating between processor 604 and system memory 606.

Depending on the desired configuration, processor 604 may be of any type including but not limited to a microprocessor (µP), a microcontroller (µC), a digital signal processor (DSP), or any combination thereof. Processor 604 may include one or more levels of caching, such as a cache memory 612, a processor core 614, and registers 616. Example processor core 614 may include an arithmetic logic unit (ALU), a floating point unit (FPU), a digital signal processing core (DSP core), or any combination thereof. An example memory controller 618 may also be used with processor 604, or in some implementations, memory controller 615 may be an internal part of processor 604.

Depending on the desired configuration, system memory 606 may be of any type including but not limited to volatile memory (such as RAM), non-volatile memory (such as ROM, flash memory, etc.) or any combination thereof. System memory 606 may include an operating system 620, one or more manufacturing control applications 622, and program data 624. Manufacturing control application 622 may include a control module 626 that may be arranged to control automated system of FIG. 5 and any other operations, functions or actions processes, methods and operations as discussed above. Program data 624 may include, among other data, material data 628 for controlling various aspects of the automated machine in system 500. This described basic configuration 602 is illustrated in FIG. 6 by those components within the inner dashed line.

Computing device 600 may have additional features or functionality, and additional interfaces to facilitate communications between basic configuration 602 and any devices and interfaces. For example, a bus/interface controller 630 may be used to facilitate communications between basic configuration 602 and one or more data storage devices 632 via a storage interface bus 634. Data storage devices 632 may be removable storage devices 636, non-removable storage devices 638, or a combination thereof. Examples of removable storage and non-removable storage devices include magnetic disk devices such as flexible disk drives and hard-disk drives (HDDs), optical disk drives such as compact disk (CD) drives or digital versatile disk (DVD) drives, solid state drives (SSDs), and tape drives to name a few. Example computer storage media may include volatile and non-volatile, removable and non-removable media implemented in any method or technology for storage of information, such as computer readable instructions, data structures, program modules, or other data.

System memory 606, removable storage devices 636 and non-removable storage devices 638 may be examples of computer storage media. Computer storage media may include, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 600. Any such computer storage media may be part of computing device 600.

Computing device 600 may also include an interface bus 640 for facilitating communication from various interface devices (e.g., output devices 642, peripheral interfaces 644, and communication devices 666) to basic configuration 602 via bus/interface controller 630. Example output devices 642 may include a graphics processing unit 648 and an audio processing unit 650, which may be configured to communicate to various external devices such as a display or speakers via one or more A/V ports 652. Example peripheral interfaces 544 may include a serial interface controller 654 or a parallel interface controller 656, which may be configured to communicate with external devices such as input devices (e.g., keyboard, mouse, pen, voice input device, touch input device, etc.) or other peripheral devices (e.g., printer, scanner, etc.) via one or more I/O ports 658. An example communication device 666 may include a network controller 660, which may be arranged to facilitate communications with one or more other computing devices 662 over a network communication link via one or more communication ports 664.

The network communication link may be one example of a communication media. Communication media may be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 600 may be implemented as a portion of a physical server, virtual server, a computing cloud, or a hybrid device that may include any of the above functions. Computing device 600 may also be implemented as a personal computer including both laptop computer and non-laptop computer configurations. Moreover computing device 600 may be implemented as a networked system or as part of a general purpose or specialized server.

Networks for a networked system including computing device 600 may comprise any topology of servers, clients, switches, routers, modems, Internet service providers, and any appropriate communication media (e.g., wired or wireless communications). A system according to embodiments may have a static or dynamic network topology. The networks may include a secure network such as an enterprise network (e.g., a LAN, WAN, or WLAN), an unsecure network such as a wireless open network (e.g., IEEE 602.11 wireless networks), or a world-wide network such (e.g., the Internet). The networks may also comprise a plurality of distinct networks that may be adapted to operate together. Such networks may be configured to provide communication between the nodes described herein. By way of example, and not limitation, these networks may include wireless media such as acoustic, RF, infrared and other wireless media. Furthermore, the networks may be portions of the same network or separate networks.

Figure 7:
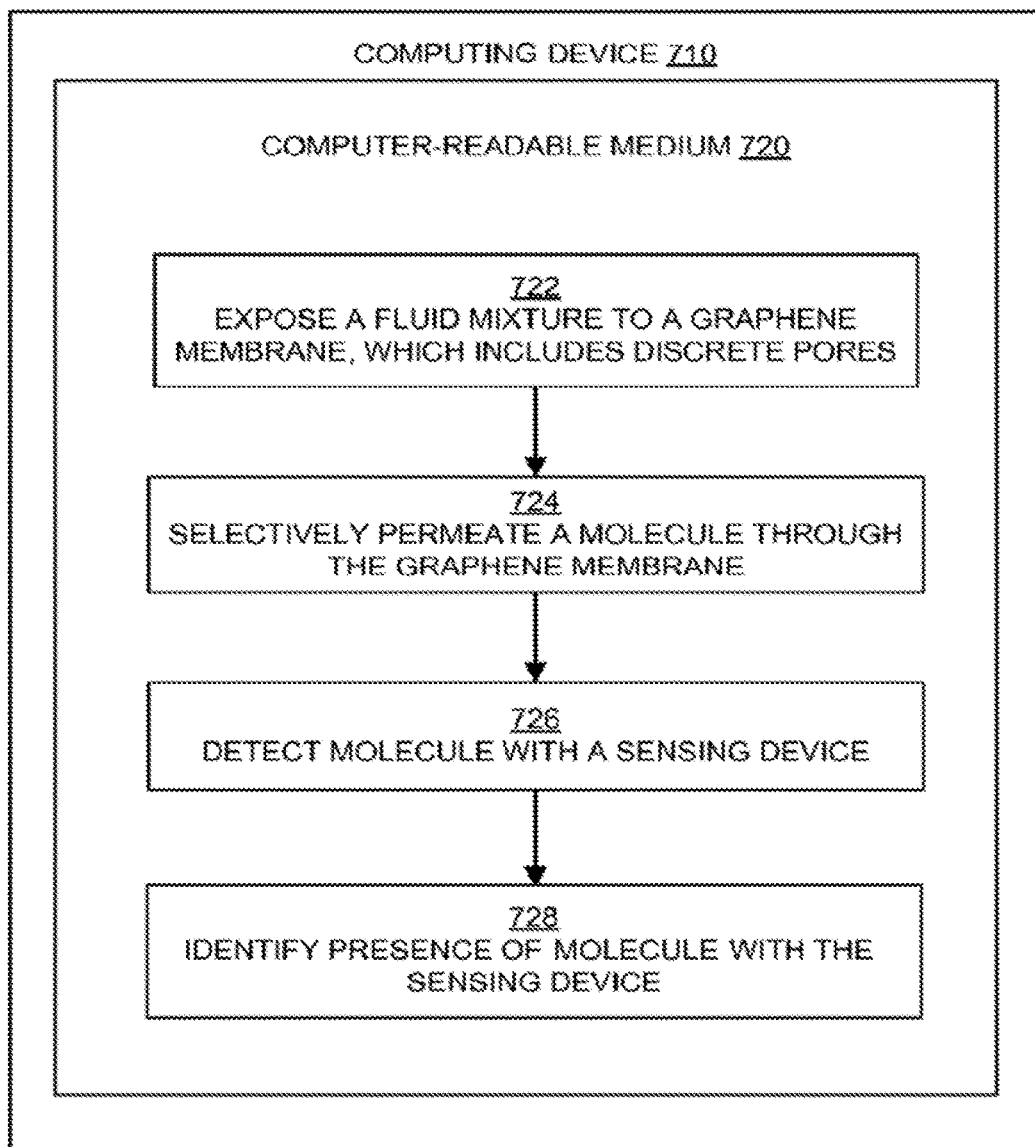
FIG. 7 is a flow diagram showing steps that may be used for detecting a gas molecule that crosses a graphene membrane.

FIG. 7 is a flow diagram illustrating a method that may be used to detect a gas molecule that crosses a graphene membrane, arranged in accordance with at least some embodiments described herein.

Example methods may include one or more operations, functions or actions as illustrated by one or more of blocks 722, 724, 726 and/or 728. The operations described in blocks 722 through 728 may also be stored as computerexecutable instructions in a computer-readable medium such as computer-readable medium 720 of computing device 710.

A process of detecting a gas molecule that crosses a graphene membrane may begin with block 722, "EXPOSE A FLUID MIXTURE TO A GRAPHENE MEMBRANE, WHICH INCLUDES DISCRETE PORES." At block 722, a fluid mixture 404 may be exposed to a graphene membrane 406, such that the fluid mixture 404 may be brought into contact with the graphene membrane 406. The fluid mixture 404 may be a mixture in a gas phase, liquid phase, or supercritical phase, and may include two or more distinct molecular species which may be separated based on properties of each species, such as size. For example, the fluid mixture 404 may include two or more molecules such that a first molecule 412 may be smaller than a second molecule 414. The graphene membrane 406 may be a graphene monolayer, which includes a plurality of discrete pores 408 having a size-selective for the passage of the first smaller gas molecule but not the second larger gas molecule.

Block 722 may be followed by block 724, "SELECTIVELY PERMEATE A MOLECULE THROUGH THE GRAPHENE MEMBRANE." When the fluid mixture 404 is exposed to and brought into contact with the graphene membrane 406, the first molecule 412 may be directed through the plurality of discrete pores 408 such that the first molecule may be separated from the second molecule 414. The first molecule 412 may be smaller than the diameter of the discrete pores 408 such that the first molecule 412 may pass through the discrete pores 408. The second molecule 414 may be larger than the diameter of the discrete pores 408 such that the second molecule may be prevented from crossing the graphene membrane through the discrete pores.

Block 724 may be followed by block 726, "DETECT MOLECULE WITH A SENSING DEVICE." A sensing device 402 may be coupled with the graphene membrane 406 in order to detect first molecule 412 when it crosses the graphene membrane 406 through the discrete pores 408. The sensing device 402 may be supported by a permeable substrate 420 and coupled with the graphene membrane by one or more electrode contacts 416 and/or an insulating frame 410.

Block 726 may be followed by block 728, "IDENTIFY PRESENCE OF MOLECULE WITH THE SENSING DEVICE." The sensing device 402 may be configured to identify a presence of the first molecule 412 that crosses the graphene membrane 406 through the discrete pores 408. In some examples, the sensing device 402 may be a rigid graphene sensor, and the rigid graphene sensor may be deposited with palladium nanoparticles in order to detect the presence of hydrogen.

FIG. 8 illustrates a block diagram of an example computer program product that may be used to control the automated machine of FIG. 5 or similar manufacturing equipment in making an example membrane, arranged in accordance with at least some embodiments described herein. In some examples, as shown in FIG. 8, computer program product 800 may include a signal bearing medium 802 that may also include machine readable instructions 804 that, when executed by, for example, a processor, may provide the functionality described above with respect to FIG. 6 and FIG. 7. Thus, for example, referring to processor 604, the control module 626 may undertake one or more of the tasks shown in FIG. 8 in response to instructions 804 conveyed to processor 604 by signal bearing medium 802 to perform actions associated with filtering a fluid mixture through a gas filtration device including a plurality of carbon nanotubes as described herein. Some of those instructions may include providing a fluid mixture to a graphene membrane including discrete pores providing size-selective access of gas molecules, contacting the fluid mixture to the graphene membrane, selectively permeating a molecule through the graphene membrane, providing a sensing device configured to detect the molecule, and detecting a presence of the molecule at the sensing device.

In some implementations, signal bearing medium 802 depicted in FIG. 8 may encompass a computer-readable medium 806, such as, but not limited to, a hard disk drive (HDD), a Compact Disc (CD), a Digital Versatile Disk (DVD), a digital tape, memory, etc. In some implementations, signal bearing medium 802 may encompass a recordable medium 808, such as, but not limited to, memory, read/write (R/W) CDs, R/W DVDs, etc. In some implementations, signal bearing medium 802 may encompass a communications medium 810, such as, but not limited to, a digital and/or an analog communication medium (e.g., a fiber optic cable, a waveguide, a wired communication link, a wireless communication link, etc.). Thus, for example, computer program product 800 may be conveyed to one or more modules of the processor 504 by an RF signal bearing medium 802, where the signal bearing medium 802 is conveyed by a wireless communications medium 810 (e.g., a wireless communications medium conforming with the IEEE 802.11 standard).

According to some examples embodiments, the present disclosure describes a gas detection device. The gas detection device may include a substrate, a sensing device coupled to the substrate, the sensing device configured to detect a presence of one or more gases, and a graphene membrane coupled to the sensing device, the graphene membrane including a plurality of discrete pores having a size-selective to pass of the one or more gases across the graphene membrane such that the sensing device may be operable to detect the presence of the one or more gases.

According to some examples, the graphene membrane may include a graphene monolayer with the plurality of discrete pores having a substantially uniform pore size. Each pore in the plurality of discrete pores may be characterized by at least one carbon vacancy defect in the graphene monolayer. Each pore in the plurality of discrete pores may be characterized by two or more carbon vacancy defects in the graphene monolayer.

According to some examples, the graphene monolayer may be characterized by selectivity to $H_2$. The graphene monolayer may be characterized by a separation selectivity of $H_2:CH_4$ of at least 200:1. The plurality of discrete pores may be characterized by a minimum separation of at least about 2.5 Angstroms. Carbon vacancy defects in the graphene monolayer may be passivated with hydrogen.

According to some examples, the substrate may include one or more of a polyethylene, polypropylene, polyester, polyurethane, polystyrene, polysulfone, polyethersulfone, $SiO_2$, SiC, and/or Si substrate. The sensing device may be one of a: metal-oxide, non-metal oxide, catalytic, optical, resistance-based, thermally conductive, work function-based, mechanical, acoustic, and electrochemical sensor configured to detect the presence of $H_2$. The sensing device may be a rigid graphene sensor, where the graphene sensor may be deposited with palladium nanoparticles for detecting the presence of $H_2$.

According to some examples, the graphene monolayer may be coupled to the sensing device by an insulating frame. The graphene monolayer may be coupled to the sensing device by one or more electrode contacts. The graphene monolayer may be coupled to the sensing device by one or more electrode contacts through an insulating frame.

According to other example embodiments, the present disclosure also describes a method of detecting a gas molecule in a fluid mixture including one or more gases. The method may include exposing the fluid mixture, which includes at least a first gas molecule and a second gas molecule to a graphene membrane such that the fluid mixture may be brought in contact with the graphene membrane, where the graphene membrane includes including a plurality of discrete pores having a size-selective for the passage of the first gas molecule but not the second gas molecule, selectively permeating the first gas molecule through the discrete pores of the graphene membrane, detecting the first gas molecule with a sensing device, and identifying the presence of the first gas molecule with sensing device.

According to some examples, the method may also include exposing the fluid mixture to a graphene monolayer, where the plurality of discrete pores may be formed in the graphene monolayer to cause one or more carbon vacancy defects in the graphene monolayer such that the graphene monolayer has substantially uniform pore sizes throughout.

According to other examples, the method may also include exposing the fluid mixture to the graphene monolayer such that there may be selective passage of $H_2$ across the graphene monolayer. Selectively permeating the first gas molecule through the discrete pores of the graphene membrane may also include permeating the first gas molecule through the plurality of discrete pores by employing a gradient across the graphene monolayer. Selectively permeating the first gas molecule through the discrete pores of the graphene membrane may also include permeating the first gas molecule through the plurality of discrete pores by employing one or more of a temperature, pressure, concentration, polarity, or electrochemical potential gradient across the graphene monolayer.

According to other examples, the method may also include separating the first gas molecule from the second gas molecule of the fluid mixture at a separation selectivity of $H_2$:$CH_4$ of at least 200:1. Detecting the first gas molecule with the sensing device may also include detecting one or more of helium, neon, argon, xenon, krypton, radon, hydrogen, nitrogen, oxygen, carbon monoxide, carbon dioxide, sulfur dioxide, hydrogen sulfide, a nitrogen oxide, a C1-C4 alkane, a silane, or a haloacid at the sensing device.

According to further example embodiments, the present disclosure also includes a method of forming a gas detection device. The method may include providing a substrate to provide support a sensing device and a graphene membrane, coupling the sensing device with the substrate, where the sensing device may be operable to detect a presence of one or more gases included in a fluid mixture, and coupling the graphene membrane with the sensing device, where the graphene membrane includes a plurality of discrete pores having a size-selective for the passage of the one or more gases across the graphene membrane for detection by the sensing device.

According to some examples, the method may also include forming the graphene membrane from a graphene monolayer with the plurality of discrete pores having a substantially uniform pore size. The method may also include forming the plurality of discrete pores in the graphene monolayer by removing graphene carbon atoms from a plurality of locations within the graphene monolayer, where the plurality of discrete pores may be characterized by a plurality of carbon vacancy defects in the graphene monolayer such that the graphene monolayer has substantially uniform pore sizes throughout. The method may also include forming the plurality of discrete pores in the graphene monolayer by causing one or more carbon vacancy defects in the graphene monolayer such that the plurality of discrete pores may be characterized by a diameter that may be selective for passage of $H_2$.

According to some examples, the method may also include passivating the one or more carbon vacancy defects in the graphene monolayer with hydrogen. Coupling the sensing device with the substrate may also include selecting the substrate from one or more of polyethylene, polypropylene, polyester, polyurethane, polystyrene, polysulfone, polyethersulfone, $SiO_2$, SiC, and/or Si substrate. The method may also include selecting the sensing device from one or more of: a metal-oxide, non-metal oxide, catalytic, optical, resistance-based, thermally conductive, work function-based, mechanical, acoustic, and electrochemical sensor. Coupling a graphene membrane with the sensing device may also include coupling the graphene membrane with the sensing device by an insulating frame.

According to some examples, coupling a graphene membrane with the sensing device further may also include coupling the graphene membrane with the sensing device by one or more electrode contacts. Coupling the sensing device with the substrate may further include positioning the sensing device within a depressed portion of the substrate. Coupling the sensing device with the substrate may also include forming the sensing device from a rigid graphene sensor. Coupling the sensing device with the substrate may further include depositing the rigid graphene sensor with Palladium particles for detecting the presence of $H_2$ at the sensing device.

According to yet other example embodiments, the present disclosure also describes a system for manufacturing a gas detection device. The system may include a controller configured by instructions stored thereon to facilitate manufacturing of the gas detection device employing a graphene source, a substrate source, and a sensing device applicator. The controller may be operable to configure the graphene source to provide a graphene membrane, where the graphene membrane includes a plurality of discrete pores having a size-selective for the passage of one or more gases included in a fluid mixture across the graphene membrane, configure the substrate source to provide a substrate to support the graphene membrane, and configure the sensing device applicator to contact a sensing device with the substrate, the sensing device configured to detect a presence of the one or more gases contained in the fluid mixture that cross the graphene membrane.

According to some examples, the controller may be further operable to configure a sample manipulator to support formation of the graphene membrane from a graphene monolayer with the plurality of discrete pores having a substantially uniform pore size. The controller may be further operable to configure a graphene perforation apparatus to form the plurality of discrete pores in the graphene monolayer by removing graphene carbon atoms from a plurality of locations within the graphene monolayer, where the plurality of discrete pores may be characterized by a plurality of carbon vacancy defects in the graphene monolayer such that the graphene monolayer has substantially uniform pore sizes throughout. The graphene perforation apparatus may be further configured to form the plurality of discrete pores in the graphene monolayer by causing one or more carbon vacancy defects in the graphene monolayer such that the plurality of discrete pores may be characterized by a diameter that may be selective for passage of $H_2$.

According to some examples, the controller may be further operable to configure a hydrogen passivation source to passivate the one or more carbon vacancy defects in the graphene monolayer with hydrogen. The substrate source may be further configured to provide one or more of a polyethylene, polypropylene, polyester, polyurethane, polystyrene, polysulfone, polyethersulfone, $SiO_2$, SiC, and/or Si substrate. The sensing device applicator may be further configured to couple one or more of: a metal-oxide, nonmetal oxide, catalytic, optical, resistance-based, thermally conductive, work function-based, mechanical, acoustic, and electrochemical sensor with the substrate. The controller may be further operable to configure a cavity apparatus to form cavity depressed cavity area on a surface of the substrate and position the sensing device within the cavity formed in the substrate.

According to some examples, the sensing device applicator may be further configured to couple a rigid graphene sensor with the substrate. The sensing device applicator may be further configured to deposit the rigid graphene sensor with palladium nanoparticles to detect the presence of $H_2$ to the substrate. The controller may be further operable to configure an electrode applicator to couple the rigid graphene sensor with the substrate by an insulating frame and electrode contacts.

There is little distinction left between hardware and software implementations of aspects of systems; the use of hardware or software is generally (but not always, in that in certain contexts the choice between hardware and software may become significant) a design choice representing cost vs. efficiency tradeoffs. There are various vehicles by which processes and/or systems and/or other technologies described herein may be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples may be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g. as one or more programs running on one or more microprocessors), as firmware, or as virtually any combination thereof, and that designing the circuitry and/or writing the code for the software and/or firmware would be well within the skill of one of skill in the art in light of this disclosure.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive (HDD), a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communication link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein may be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity of gantry systems; control motors for moving and/or adjusting components and/or quantities).

A typical data processing system may be implemented utilizing any suitable commercially available components, such as those typically found in data computing/communication and/or network computing/communication systems. The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically connectable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A gas detection device, comprising:
   a substrate, wherein a portion of a surface of the substrate is depressed to form a cavity in the surface of the substrate;
   a sensor device comprising a rigid graphene sensor deposited with palladium nanoparticles, wherein the sensor device:
   is coupled to the substrate and positioned within the cavity,
   is confined below the surface of the substrate by being positioned within the cavity,
   is configured to detect a presence of hydrogen, and
   has a sensitivity, to detect the presence of the hydrogen, that is reduced in response to the sensor device being subjected to contamination from methane; and
   a graphene membrane coupled to the sensor device by at least one of an insulation frame and one or more electrode contacts, wherein:
   the graphene membrane includes a graphene monolayer with a plurality of discrete pores having a size-selectivity based on a diameter of each of the plurality of discrete pores for passage of the hydrogen across the graphene membrane for detection by the sensor device, and having the size-selectivity for inhibition of passage of the methane across the graphene membrane so as to restrict the methane from contact with the sensor device and thus to protect the sensor device from the contamination that reduces the sensitivity of the sensor device to detect the presence of the hydrogen,
   the diameter of each of the plurality of discrete pores of the graphene membrane is 2.5 Angstroms, and a hydrogen and methane separation selectivity of the graphene membrane is $10^{23}:1$ based on the diameter of each of the plurality of discrete pores, the hydrogen is selectively permeated through the discrete pores of the graphene monolayer by employment of a gradient across the graphene monolayer, and the gradient includes one or more of a temperature gradient, a pressure gradient, a concentration gradient, a polarity gradient, and an electrochemical potential gradient.

2. The gas detection device of claim 1, wherein the plurality of discrete pores have a uniform pore size.

3. The gas detection device of claim 2, wherein each pore in the plurality of discrete pores includes eat least one carbon vacancy defect in the graphene monolayer.

4. The gas detection device of claim 2, wherein each pore in the plurality of discrete pores includes two or more carbon vacancy defects in the graphene monolayer.

5. The gas detection device of claim 2, wherein carbon vacancy defects in the graphene monolayer are passivated with hydrogen.

6. The gas detection device of claim 1, wherein the substrate includes one or more of a polyethylene, polypropylene, polyester, polyurethane, polystyrene, polysulfone, polyethersulfone, $SiO_2$, SiC, and/or Si substrate.

7. The gas detection device of claim 1, wherein the sensor device is selected from one of a: metal-oxide, non-metal oxide, catalytic, optical, resistance-based, thermally conductive, work function-based, mechanical, acoustic, and electrochemical sensor configured to detect the presence of hydrogen.

8. A system to manufacture a gas detection device, the system comprising:

a controller communicatively coupled to a graphene source that provides a graphene membrane, a substrate source that provides a substrate, and a sensor device applicator, wherein the controller is configured to:

instruct the graphene source to provide the graphene membrane, wherein:

the graphene membrane includes a graphene monolayer with a plurality of discrete pores having a size-selectivity based on a diameter of each of the plurality of discrete pores for passage of hydrogen across the graphene membrane for detection by a sensor device, and having the size-selectivity for inhibition of passage of methane across the graphene membrane so as to restrict the methane from contact with the sensor device and thus to protect the sensor device from contamination that reduces a sensitivity of the sensor device to detect a presence of the hydrogen, the diameter of each of the plurality of discrete pores of the graphene membrane is 2.5 Angstroms, and a hydrogen and methane separation selectivity of the graphene membrane is 10^23:1 based on the diameter of each of the plurality of discrete pores, the hydrogen is selectively permeated through the discrete pores of the graphene monolayer by employment of a gradient across the graphene monolayer, and the gradient includes one or more of a temperature gradient, a pressure gradient, a concentration gradient, a polarity gradient, and an electrochemical potential gradient;

instruct the substrate source to provide the substrate to support the graphene membrane, wherein a portion of a surface of the substrate is depressed to form a cavity in the surface of the substrate; and instruct the sensor device applicator to position the sensor device within the cavity of the surface of the substrate, wherein the sensor device is confined below the surface of the substrate by being positioned within the cavity, wherein the sensor device is configured to detect the presence of the hydrogen that crosses the graphene membrane, and wherein the sensor device comprises a rigid graphene sensor deposited with palladium nanoparticles to detect the presence of the hydrogen.

9. The system of claim 8, wherein the controller is further configured to:

instruct a sample manipulator to support formation of the graphene membrane from the graphene monolayer with the plurality of discrete pores, which have a uniform pore size.

10. The system of claim 9, wherein the controller is further configured to:

instruct a graphene perforation apparatus to form the plurality of discrete pores in the graphene monolayer by removal of graphene carbon atoms from a plurality of locations within the graphene monolayer, wherein the plurality of discrete pores include a plurality of carbon vacancy defects in the graphene monolayer such that the graphene monolayer has uniform pore sizes throughout.

11. The system of claim 10, wherein the graphene perforation apparatus is further configured to:

form the plurality of discrete pores in the graphene monolayer by causing one or more of the plurality of carbon vacancy defects in the graphene monolayer by employment of one or more of: UV-induced oxidative etching, ion beam etching, and/or lithographic masking coupled with oxygen plasma etching such that the plurality of discrete pores have the diameter that is selective for the passage of the hydrogen.

12. The system of claim 11, wherein the controller is further configured to:

instruct a hydrogen passivation source to passivate the one or more of the plurality of carbon vacancy defects in the graphene monolayer with hydrogen.

13. The system of claim 11, wherein the controller is further configured to:

instruct an apparatus to form the cavity in the surface of the substrate.

14. The system of claim 8, wherein the controller is further configured to:

instruct an electrode applicator to couple the sensor device with the substrate by an insulation frame and electrode contacts.

* * * * *

UNITED STATES PATENT AND TRADEMARK OFFICE
CERTIFICATE OF CORRECTION

| | | |
|---|---|---|
| PATENT NO. | : 9,759,700 B2 | Page 1 of 1 |
| APPLICATION NO. | : 14/005232 | |
| DATED | : September 12, 2017 | |
| INVENTOR(S) | : Sjong et al. | |

It is certified that error appears in the above-identified patent and that said Letters Patent is hereby corrected as shown below:

In the Claims

In Column 20, Line 47, in Claim 1, delete "methane; and" and insert -- methane; --, therefor.

In Column 20, Line 67, in Claim 1, delete "pores," and insert -- pores; and --, therefor.

In Column 21, Line 1, in Claim 1, delete "the hydrogen is" and insert -- a processor configured to allow the hydrogen to be --, therefor.

In Column 21, Lines 3-4, in Claim 1, delete "monolayer, and" and insert -- monolayer, wherein: --, therefor.

In Column 21, Line 12, in Claim 3, delete "eat least" and insert -- at least --, therefor.

In Column 21, Line 56, in Claim 8, delete "the hydrogen is" and insert -- a processor is configured to allow the hydrogen to be --, therefor.

Signed and Sealed this
Eighth Day of May, 2018

Andrei Iancu
*Director of the United States Patent and Trademark Office*